United States Patent
Pan et al.

(10) Patent No.: US 11,214,806 B2
(45) Date of Patent: Jan. 4, 2022

(54) MARKER, METHOD AND KIT FOR OBSERVING EFFECT OF COMPOUND OR DRUG ON CELLS IN REAL TIME, AND USE THEREOF

(71) Applicant: Foshan University, Foshan (CN)

(72) Inventors: Shen Quan Pan, Beijing (CN); Qinghua Yang, Singapore (SG); Xiaoyang Li, Singapore (SG); Haitao Tu, Singapore (SG)

(73) Assignee: Foshan University, Foshan (CN)

( * ) Notice: Subject to any disclaimer, the term of this patent is extended or adjusted under 35 U.S.C. 154(b) by 0 days.

(21) Appl. No.: 16/467,948

(22) PCT Filed: Dec. 9, 2016

(86) PCT No.: PCT/CN2016/109175
§ 371 (c)(1),
(2) Date: Jun. 7, 2019

(87) PCT Pub. No.: WO2018/103067
PCT Pub. Date: Jun. 14, 2018

(65) Prior Publication Data
US 2020/0063145 A1    Feb. 27, 2020

(51) Int. Cl.
*C12N 15/65* (2006.01)
*C12N 15/82* (2006.01)
*G01N 33/50* (2006.01)

(52) U.S. Cl.
CPC ............. *C12N 15/65* (2013.01); *C12N 15/82* (2013.01); *G01N 33/5008* (2013.01)

(58) Field of Classification Search
None
See application file for complete search history.

(56) References Cited

U.S. PATENT DOCUMENTS

2012/0202971 A1    8/2012    Kent et al.

OTHER PUBLICATIONS

Li et al (The Plant Journal, 77:487-498, 2014).*
Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Li et al (Plant J., 77:487-495, 2014).*
Ghosh, I.N. et al., "Superfolder GFP [Cloning Vec tor pRH52]", GenBank: A0H95447.1, Sep. 6, 2016, complete sequences, 1 page.
Oger, P.M. et al., "VirE2 (Plasmid) [Agrobacterium Tumefaciens]", GenBank: AAZ50538.1, Jul. 26, 2016, complete sequences, 1 page.
Miller, K.E. et al., "Bimolecular Fluorescence Complementarian (BiFC) Analysis: Advances and Recent Applications for Genome-Wide Interaction Studies", JMB, vol. 427, Dec. 31, 2015, abstract, 28 pages.
Sakalis, P.A. et al., "Visualization of VirE2 Protein Translocation by the Agrbacterium Type IV Secretion System into Host Cells", Microbiology Open, 3(1), Dec. 31, 2014, abstract, p. 105, right-hand column, paragraph 6 to p. 113, left-hand column, paragraph 1, and figures 1-7, 14 pages.
Equbal, M.J. et al., "Superfolder Green Fluorescent Protein [Synthetic construct]", GenBank: ADW83736.1, Feb. 9, 2011, complete sequences, 1 page.
Venengelenburg, S.B. et al., "Imaging Type-III Secretion Reveals Dynamics and Spatial Secretation of *Salmonella* Effectors", Nat. Methods, 4(7), Apr. 30, 2010, abstract, and p. 8, paragraph 2, 20 pages.
Kerppola, T.K., "Design and Implementation of Bimolecular Fluorescence Complementation (BiFC) Assays for the Visualization of Protein Interactions in Living Cells", Nature Protocols, 1(3), Oct. 5, 2006, abstract, p. 1279, table 1, and p. 1280, left-hand column, paragraph 1, 10 pages.
Cabantous, S. et al., "Protein Tagging and Detection with Engineered Self-Assembling Fragments of Green Fluorescent Protein", Nature Biotechnology, 23(1), Dec. 5, 2004, abstract, p. 102, and supplementary table 1, 6 pages.
Atmakuri, K. et al., "VirE2, a Type IV Secretion Substrate, Interacts with the VirD4 Transfer Protein at Cell Poles of Agrobacterium Tumefaciens", Molecular Microbiology, 496), Dec. 31, 2003, pp. 1699-1713, 25 pages.
Zhou, X.R. et al., "Mutagenesis of the Agrobacterium VirE2 Single-Stranded DNA-Binding Protein Identifies Regions Required for Self-Association and Interaction with VirE1 and a Permissive Site for Hybrid Protein Construction", Journal of Bacteriology, 181(14), Jul. 31, 1999, pp. 4342-4352, 11 pages.

* cited by examiner

*Primary Examiner* — Brian Gangle
(74) *Attorney, Agent, or Firm* — Inskeep IP Group, Inc.

(57) ABSTRACT

Disclosed is a marker for observing an effect of a compound or a drug on cells in real time. The marker is: 1) an amino acid sequence shown in SEQ No. 1 and/or SEQ No. 2; or 2) an amino acid sequence having a function for observing an effect of a compound or a drug on cells in real time and having at least more than 80%, preferably more than 85%, more preferably 90%, further preferably 95%, and most preferably 99% homology with the amino acid sequence shown in SEQ No. 1 and/or SEQ No. 2. Also disclosed is a method and a kit for observing an effect of a compound or a drug on cells in real time and use thereof.

4 Claims, 11 Drawing Sheets
Specification includes a Sequence Listing.

SEQUENCE LISTING

```
<160> NUMBER OF SEQ ID NOS: 2

<210> SEQ ID NO 1
<211> LENGTH: 565
<212> TYPE: PRT
<213> ORGANISM: Artificial Sequence
<220> FEATURE:
<223> OTHER INFORMATION: VirE2-GFP11

<400> SEQUENCE: 1

Met Asp Pro Ser Ser Asn Glu Asn Val Tyr Val Gly Arg Gly His Asn
1               5                   10                  15

Ile Glu Asn Asp Asp Thr Asp Pro Arg Arg Trp Lys Lys Ala Asn
            20                  25                  30

Ile Ser Ser Asn Thr Ile Ser Asp Ile Gln Met Thr Asn Gly Glu Asp
        35                  40                  45

Val Gln Ser Gly Ser Pro Arg Asp His Met Val Leu His Glu Tyr Val
    50                  55                  60

Asn Ala Ala Gly Ile Thr Thr Arg Thr Glu Val Val Ser Pro Arg Leu
65                  70                  75                  80

Asp Tyr Gly Ser Val Asp Ser Ser Ser Leu Tyr Ser Gly Ser Glu
                85                  90                  95

His Gly Asn Gln Ala Glu Ile Gln Lys Glu Leu Ser Val Leu Phe Ser
            100                 105                 110

Asn Met Ser Leu Pro Gly Asn Asp Arg Arg Pro Asp Glu Tyr Ile Leu
        115                 120                 125

Val His Gln Thr Gly Gln Asp Ala Phe Thr Gly Ile Ala Lys Gly Asn
    130                 135                 140

Leu Asp Gln Met Pro Thr Lys Ala Glu Phe Asn Ala Cys Cys Arg Leu
145                 150                 155                 160

Tyr Arg Asp Gly Ala Gly Asn Tyr Tyr Pro Pro Pro Leu Ala Phe Asp
                165                 170                 175

Lys Ile Ser Val Pro Glu Gln Leu Glu Glu Lys Trp Gly Met Met Glu
            180                 185                 190

Ala Lys Glu Arg Asn Lys Leu Arg Phe Gln Tyr Lys Leu Asp Val Trp
        195                 200                 205

Asn His Ala His Ala Asp Met Gly Ile Thr Gly Thr Glu Ile Phe Tyr
```

```
                    210                 215                 220
Gln Thr Asp Lys Asn Ile Lys Leu Asp Arg Asn Tyr Lys Leu Arg Pro
225                 230                 235                 240

Glu Asp Arg Tyr Val Gln Thr Glu Lys Tyr Gly Arg Arg Glu Ile Gln
                245                 250                 255

Lys Arg Tyr Gln His Glu Leu Gln Ala Gly Ser Leu Leu Pro Asp Ile
                260                 265                 270

Met Ile Lys Thr Pro Gln Asn Asp Ile His Phe Val Tyr Arg Phe Ala
            275                 280                 285

Gly Asp Asn Tyr Ala Asn Lys Gln Phe Ser Glu Phe Glu His Thr Val
        290                 295                 300

Lys Arg Arg Tyr Gly Asp Glu Thr Glu Ile Lys Leu Lys Ser Lys Ser
305                 310                 315                 320

Gly Ile Met His Asp Ser Lys Tyr Leu Glu Ser Trp Glu Arg Gly Ser
                325                 330                 335

Ala Asp Ile Arg Phe Ala Glu Phe Val Gly Glu Asn Arg Ala His Asn
                340                 345                 350

Arg Gln Phe Pro Thr Ala Thr Val Asn Met Gly Gln Gln Pro Asp Gly
            355                 360                 365

Gln Gly Gly Leu Thr Arg Asp Arg His Val Ser Val Asp Phe Leu Met
        370                 375                 380

Gln Ser Ala Pro Asn Ser Pro Trp Ala Gln Ala Leu Lys Lys Gly Glu
385                 390                 395                 400

Leu Trp Asp Arg Val Gln Leu Leu Ala Arg Asp Gly Asn Arg Tyr Leu
                405                 410                 415

Ser Pro Pro Arg Leu Glu Tyr Ser Asp Pro Ala His Phe Thr Glu Leu
                420                 425                 430

Met Asn Arg Val Gly Leu Pro Ala Ser Met Gly Arg Gln Ser His Ala
            435                 440                 445

Ala Ser Ile Lys Phe Glu Lys Phe Asp Ala Gln Ala Ala Val Ile Val
        450                 455                 460

Leu Asn Gly Pro Glu Leu Arg Asp Ile His Asp Leu Ser Pro Glu Lys
465                 470                 475                 480

Leu Gln Asn Leu Ser Thr Lys Asp Val Ile Val Ala Asp Arg Asn Glu
                485                 490                 495

Asn Gly Gln Arg Thr Gly Thr Tyr Thr Ser Val Ala Glu Tyr Glu Arg
                500                 505                 510

Leu Gln Leu Arg Leu Pro Pro Asp Ala Ala Gly Val Leu Gly Glu Ala
            515                 520                 525

Thr Asp Lys Tyr Ser Arg Asp Phe Val Arg Pro Glu Pro Ala Ser Arg
        530                 535                 540

Pro Ile Ser Asp Ser Arg Arg Ile Tyr Glu Ser Arg Pro Arg Ser Gln
545                 550                 555                 560

Ser Val Asn Ser Phe
                565

<210> SEQ ID NO 2
<211> LENGTH: 215
<212> TYPE: PRT
<213> ORGANISM: Artificial Sequence
<220> FEATURE:
<223> OTHER INFORMATION: GFP1-10

<400> SEQUENCE: 2

Met Val Ser Lys Gly Glu Glu Leu Phe Thr Gly Val Val Pro Ile Leu
```

-continued

```
1               5                   10                  15
Val Glu Leu Asp Gly Asp Val Asn Gly His Lys Phe Ser Val Arg Gly
            20                  25                  30

Glu Gly Glu Gly Asp Ala Thr Ile Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Lys Tyr Lys Thr Arg Ala Val
            100                 105                 110

Val Lys Phe Glu Gly Asp Thr Leu Val Asn Arg Ile Glu Leu Lys Gly
            115                 120                 125

Thr Asp Phe Lys Glu Asp Gly Asn Ile Leu Gly His Lys Leu Glu Tyr
    130                 135                 140

Asn Phe Asn Ser His Asn Val Tyr Ile Thr Ala Asn Lys Gln Lys Asn
145                 150                 155                 160

Gly Ile Lys Ala Asn Phe Thr Val Arg His Asn Val Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Thr Val Leu
            195                 200                 205

Ser Lys Asp Pro Asn Glu Lys
    210                 215
```

MARKER, METHOD AND KIT FOR OBSERVING EFFECT OF COMPOUND OR DRUG ON CELLS IN REAL TIME, AND USE THEREOF

RELATED APPLICATIONS

This application is the U.S. National Phase of and claims priority to International Patent Application No. PCT/CN2016/109175, International Filing Date Dec. 9, 2016, entitled Marker, Method And Kit For Observing Effect Of Compound Or Drug On Cells In Real Time, And Use Thereof which is incorporated herein by reference in its entirety.

A sequence listing entitled

Jiaquan 506 2020-11-02 REVISED SEQUENCE LISTING.txt, 7,168 bytes, created on Nov. 2, 2020, 12:34 PM, is incorporated by reference in this application.

FIELD OF THE INVENTION

The present invention belongs to the field of biology. More particularly, the present invention relates to a marker for observing an effect of a compound or a drug on cells in real time, and a method and a kit for observing an effect of a compound or a drug on cells in real time by using the marker, and use thereof.

BACKGROUND OF THE INVENTION

In the process of drug development and biological research, it is very important to study the effect of a molecule or a drug on cells. This is usually realized by observing the overall healthy condition of the cells, such as death or replication rate. The study on the effect of a molecule or a drug in this way only estimates a final result using the molecule or the drug, which may miss the effect of the molecule or the drug on the cells in a continuous process. In reality, a molecule or a drug is usually used for treating an aspect of cells or life, which is a continuous process before death or replication. Therefore, current methods for studying the effect of a molecule or a drug on cells are non-real-time, indirect or inaccurate. So far, there is no method for studying the real-time effect of a molecule or a drug on cells.

For any useful molecules, such as drugs, to be commercialized, side effects or toxicity must be tested. Generally, the tests can be conducted on animals, which can be very expensive and time consuming. In addition, people advocating animal rights also object to the drug tests on animals. Therefore, there is an urgent need for a sensitive method that can quickly provide a result without using animals to test the real-time effect.

SUMMARY OF THE INVENTION

Based on the demands and deficiencies of the prior art above, an objective of the present invention is to provide a marker for observing an effect of a compound or a drug on cells in real time; another objective of the present invention is to provide a method for observing an effect of a compound or a drug on cells in real time; another objective of the present invention is to provide a kit for observing an effect of a compound or a drug on cells in real time; and another objective of the present invention is to provide a method for observing a nonspecific toxicity of a compound or a drug in real time.

In order to achieve the objectives above, the following technical solutions are used in the present invention:

In one aspect, the present invention provides a marker for observing an effect of a compound or a drug on cells in real time, wherein the marker is: 1) an amino acid sequence shown in SEQ ID NO:1 and/or SEQ ID NO:2; or 2) an amino acid sequence having a function for observing an effect of a compound or a drug on cells in real time and having at least more than 80%, preferably more than 85%, more preferably 90%, further preferably 95%, and most preferably 99% homology with the amino acid sequence shown in SEQ ID NO:1 and/or SEQ ID NO:2.

Preferably, the cells are selected from plant cells, yeasts, fungi, green algae or animal cells.

Further preferably, the effect is a nonspecific toxicity of the compound or the drug.

Further preferably, the observing an effect of a compound or a drug on cells in real time is to observe an movement of a VirE2-GFP on endoplasmic reticulum/actin network in real time.

Further preferably, the marker is a nucleotide encoding the marker.

In another aspect, the present invention provides a method for observing an effect of a compound or a drug on cells in real time, and the method comprises the following steps of:

1) introducing a marker for observing the effect of a compound or a drug on cells in real time or the marker above-mentioned to the cells, or enabling the cells to contain a marker for observing an effect of a compound or a drug on cells in real time or the marker above-mentioned;

2) adding the compound or the drug into the cells; and 3) observing a morphology, a movement track and/or a speed of the marker in the cells in real time.

Preferably, the cells are selected from plant cells, yeasts, fungi, green algae or animal cells.

More preferably, the morphology of the marker in the step 3) comprises a size, a shape, a movement mode and/or a position of a filamentous structure formed by the VirE2-GFP.

Further preferably, the observing an effect of a compound or a drug on cells in real time is to observe a movement of the VirE2-GFP on endoplasmic reticulum/actin network in real time.

Further preferably, the compound is a nucleotide and/or the drug is a small molecule drug.

More preferably, the compound or the drug is selected from a colchicine, a cytochalasin D, a Brefeldin A, an ML-7, an RFD-MBD, an MBD, an ER-mCherry, an ABD and a tail fragment of a myosin.

Further preferably, the effect is a nonspecific toxicity of the compound or the drug.

In another aspect, the present invention provides a kit for observing an effect of a compound or a drug on cells in real time, the cells are preferably selected from plant cells, yeasts, fungi, green algae or animal cells, and the kit contains a marker for observing an effect of a compound or a drug on cells in real time or the marker above-mentioned.

Preferably, the compound is a nucleotide and/or the drug is a small molecule drug.

More preferably, the compound or the drug is selected from a colchicine, a cytochalasin D, a Brefeldin A, an ML-7, an RFD-MBD, an MBD, an ER-mCherry, an ABD and a tail fragment of a myosin.

Further preferably, observing an effect of a compound or a drug on cells in real time is to observe a movement of a VirE2-GFP on endoplasmic reticulum/actin network in real time.

Further preferably, the effect is a nonspecific toxicity of the compound or the drug.

In another aspect, the present invention provides a method for observing a nonspecific toxicity of a compound or a drug in real time, and the method comprises the step of: using the marker above-mentioned and/or the kit above-mentioned.

According to the basic technical solutions of the present invention above, the concept of the present invention is further illustrated as follows.

The present invention has developed a method that can observe a real-time process of a whole movement of a protein (VirE2-GFP) generated in bacterial cells, delivered into a eukaryotic cytoplasm, and then moved to a cell nucleus. The whole process can be observed under a natural condition in real time. When a molecule or a drug is added to the test system, a real-time effect of the molecule or the drug on a movement process of cells or proteins can be directly observed.

Several compounds are tested in the present invention, some of which are drugs. The inventor finds that oral drugs on the market do not affect a real-time movement process of the protein VirE2-GFP, while toxic compounds can significantly interfere with the movement process of the protein VirE2-GFP.

Therefore, the present invention develops a technology that can directly observe a real-time effect of any compound or drug on cells, including a nonspecific toxicity. This may become an innovative drug research and development technology, and the technology can discover a nonspecific (or toxic) effect of a candidate drug at an early stage. In this way, drug development companies can evaluate a side effect and toxicity of any candidate drug as early as possible, thus saving time and money for drug development. The present invention also provides a platform for the public to directly and quickly evaluate the toxicity and non-specificity of any drug. This also helps to build confidence in drug testing for the public.

Method

The present invention develops a cell-based system which includes both bacterial cells and eukaryotic cells. A split-GFP approach is adopted to visualize an Agrobacterium-produced protein VirE2, which can be naturally delivered by Agrobacterium into eukaryotic cells. To visualize VirE2 delivered into eukaryotic cells, the small GFP fragment (GFP11) is inserted into VirE2 at a permissive site to create VirE2-GFP11 fusion, which is expressed in *A. tumefaciens*; and the large fragment (GFP1-10) is expressed in recipient cells. Upon delivery of VirE2-GFP11 into the recipient cells, GFP fluorescence signals are visualized. VirE2-GFP11 is functional like VirE2; the GFP fusion movement could indicate the trafficking of Agrobacterium-delivered VirE2.

This system can be used to visualize the entire movement of a protein produced in a bacterial cell, delivered onto a eukaryotic cytoplasm, and then moved into the nucleus. The entire process can be visualized in real time in natural setting. When a compound is added into the testing system, the effect of the compound on any of the protein trafficking process can be visualized directly.

VirE2 has the ability to aggregate to filamentous structures, which can move smoothly inside the cells. They can be easily visualized and documented. Any effect on the cells would affect the sizes, shapes, movement patterns and locations of the VirE2 filaments. This makes the test particularly sensitive.

Result

Several compounds are tested in the present invention, some of which are drugs. The inventor finds that oral drugs on the market are less toxic and do not affect a real-time movement process of a protein, while toxic compounds can significantly interfere with the movement process of a protein.

The test system covers all cell positions and all important biochemical processes. The test is very sensitive and can detect any potential nonspecific reaction. The test is very quick and can be completed in two days.

Analysis

Therefore, the present invention develops a technology that can directly visualize the non-specific effects of any drugs in real time. This can potentially revolutionize drug discovery process by revealing the non-specific (or toxic) effects of drug candidates at early stage. In this way, drug development companies can assess the side-effects and toxicity for any drug candidates as early as possible to save the time and money for drug development. It also provides a platform for the public to assess the toxicity and non-specificity of any drug in a direct and quick manner. This is certainly useful for the public to build up the confidence for drug testing.

Conclusion

The present invention develops a technology that makes it visible to test the non-specific or toxic effects of any drugs. The test can provide a mechanistic view of the nonspecific or toxic effect directly. This can quickly test whether drug candidates have potential non-specific or toxic effect at the early stage so that time and money can be saved for drug discovery.

The safety of a drug can be evaluated in a visual and understandable manner so that the public confidence on the drug can be improved. The testing system can help biological researchers to conduct mechanistic studies on any molecule. The technology can be used to develop an un-biased service center to test the potential non-specific or toxic effects of drug candidates and existing drugs on the markets.

In addition, the present invention can also be used for observing an effect of a compound or a drug on cells in real time, thus helping basic research.

BRIEF DESCRIPTION OF THE DRAWINGS

The embodiments of the present invention are described in detail hereinafter with reference to the drawings, wherein.

DETAILED DESCRIPTION OF THE EMBODIMENTS

Scheme

Figure 1:
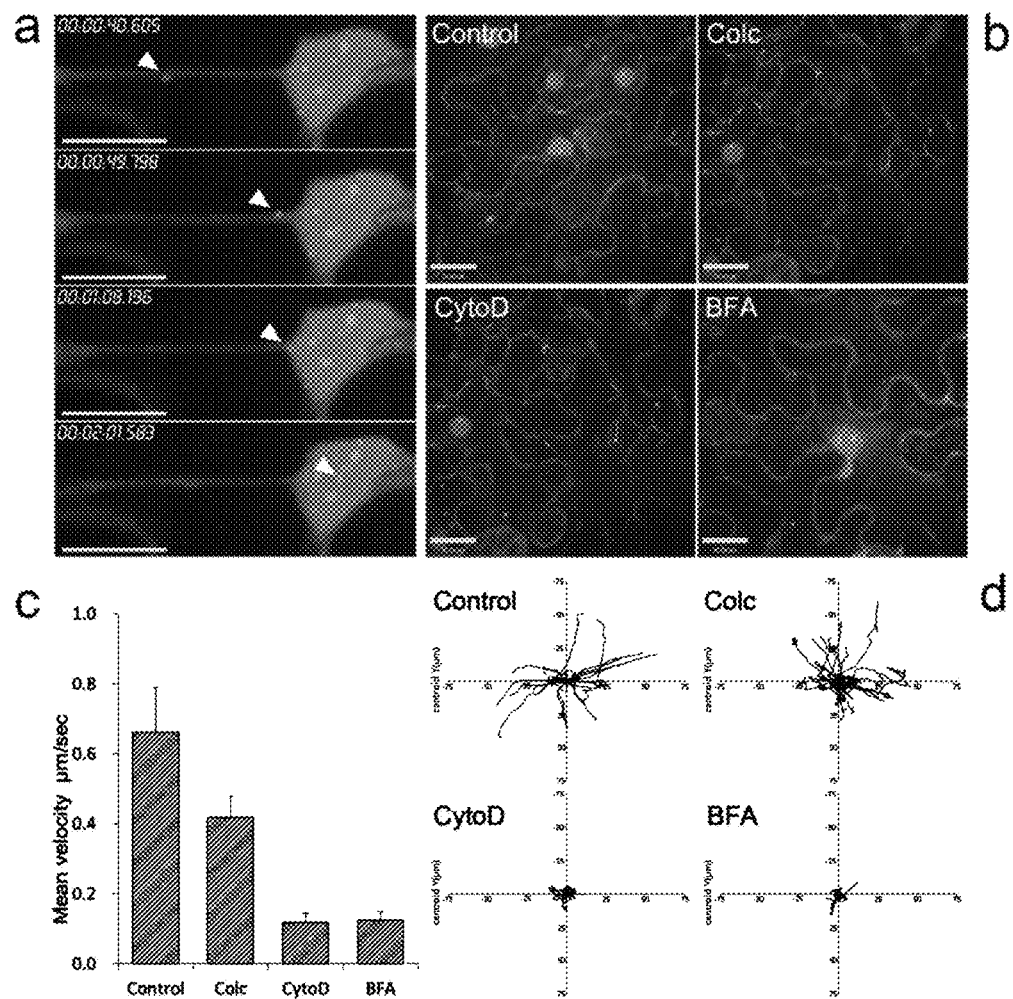
FIG. 1A is a sequence of images of VirE2 aggregates trafficking along a linear cellular structure and entering the nucleus.
FIG. 1B is a sequence of images showing effects of chemical treatments on VirE2 trafficking.
FIG. 1C is a graph representing mean velocities of VirE2 aggregate movement after chemical treatments.
FIG. 1D is a series of graphs showing effect of 20 individual VirE2 trafficking after chemical treatment.

As a soil-borne phytopathogen, *A. tumefaciens* is capable of inter-kingdom transfer of genetic materials. It can deliver single-stranded (ss) DNA (T-DNA) through a VirB/D4 type IV secretion system (T4SS) into various recipient cells. Although plant species are the natural hosts for this T-DNA transfer, other eukaryotic species can nevertheless be transformed under laboratory conditions, including yeast, fungal and algal cells, in the presence of plant wound signal compounds, such as acetosyringone. The ability of *Agrobacterium* to genetically modify recipient cells is widely used for plant and fungal transformation.

The T4SS are found both in Gram-negative and Gram-positive bacteria; they secret proteins and nucleoprotein complexes into recipient cells. *A. tumefaciens* T4SS apparatus is encoded by the vir genes on the Ti plasmid; it comprises 12 types of toxic proteins (virB1 to virB11 and virD4). During the transfer process, T-DNA is nicked and processed from T-region on the Ti-plasmid by VirD1-VirD2 endonuclease inside the bacteria. The nucleoprotein complex formed by VirD2 and T-DNA is then translocated through the T4SS to recipient cells, along with other virulence proteins, like VirD5, VirE2, VirE3 and VirF. In the recipient cell, these translocated proteins act as virulence effectors to facilitate the transformation process.

VirE2 is the most abundant among the bacterium-encoded Vir proteins. VirE2 can bind to T-DNA in a cooperative manner; it plays the critical role of protecting T-DNA from nucleolytic degradation during cytoplasmic trafficking inside the host cells. This occurs as VirE2 has the natural ability to bind to ss DNA and to self-aggregate to form solenoid super structures. VirE2 contains nuclear localization signals (NLS) that facilitate the nuclear import of VirE2 and potentially the T-DNA. There is evidence to suggest that VirE2-T-DNA interaction also plays a role in targeting the T-DNA into the nucleus, independent of the nuclear targeting activity of VirD2 which also contains the NLS. Although ectopic expression of VirE2 showed a predominant cytoplasmic localization of VirE2 in various types of plant cells, we found that using a split-GFP approach, a significant amount of *Agrobacterium*-delivered VirE2 was localized inside the plant nuclei under natural infection conditions. Indeed it is of significance to study the trafficking process of VirE2 in the cytoplasm of host cells in order to understand the transformation mechanism.

As VirE2 aggregates as the solenoid structure, its large size would strongly restrict it from reaching the host nuclei through a dense structure of cytoplasm by Brownian diffusion; there should be an active mechanism for VirE2 trafficking inside the plant cells. Previous studies showed that the interaction of VirE2 with a transcription factor VIP1 may facilitate VirE2 nuclear targeting by abusing the MAPKtargeted VIP1 defense signaling pathway. However, the role of VIP1 in *Agrobacterium*-mediated transformation is debatable. Nevertheless, it is not clear how any of the bacterial effectors and their host partners is trafficked inside host cells to facilitate the transformation.

An in vitro study showed that the presence of "animalized" VirE2, in which the VirE2 NLS was modified to become a bipartite NLS similar to nucleoplasmin, invoked active transport along microtubules in a cell-free *Xenopus* egg extract. Since microtubules are projected radially from the centrosome in animal cells, this trafficking mechanism would effectively transport nuclear-targeted cargo close to the nuclear envelope for import. Ectopically expressed VirE2 in yeast was also reported to co-localize and physically interact with microtubules. These lines of evidence suggest the involvement of microtubules in VirE2 trafficking. However, unlike animals and fungi, flowering plants lack retrograde transporter-dyneins. Moreover, plant microtubules lack conspicuous organizing centers; their arrangements are fundamentally different from the animal, fungal and protistan counterparts; microtubules may not be ideal for trafficking towards plant nuclei. Thus, it is not clear whether plant microtubules play any role in VirE2 trafficking towards the nucleus in a natural setting.

So far no natural system has been used to study the trafficking of VirE2 or any of the T-complex components; and conclusions based on in vitro experiments also have great limitations. Consequently, it is still unknown what kind of host network drives the trafficking of T-complex inside plant cells.

The present invention develops a split-GFP-based method that can directly detect the *Agrobacterium*-delivered VirE2 inside plant cells. This split-GFP approach enabled us to visualize VirE2 trafficking in the recipient cells in real-time in a natural setting. The inventor found that *Agrobacterium* transformed plant cells at a high efficiency up to 100%. The experimental results of the present invention showed that VirE2 was trafficked through myosin-powered ER/actin network inside plant cells. Since actin network is well conserved, our data suggest that *Agrobacterium* hijacks host fundamental infrastructure to achieve both the high efficiency and the wide host range for the transformation.

Result

*Agrobacterium*-delivered VirE2 moved on a strand-like cellular structure

The inventor has successfully observed that *Agrobacterium*-delivered VirE2 inside plant host cells using the split green fluorescence protein (split-GFP) method. According to the present invention, *A. tumefaciens* cells (EHA105virE2::GFP11), encoding VirE2-GFP11 fusion, are infiltrated into the leaf tissues of tobacco plants (Nb308A), which constitutively express GFP1-10 and the free DsRed that indicates the cellular structures and the nucleus. Upon delivery into plant cells by the bacterium, VirE2-GFP11 complemented GFP1-10, the resulting VirE2-GFP$_{comp}$ signals were found inside plant cells. At 2 days after agroinfiltration, VirE2-GFP$_{comp}$ aggregates started to appear, as VirE2 can aggregate to form filamentous structures.

As shown in FIG. 1a, VirE2-GFP$_{comp}$ signals moved on a strand-like cellular structure illustrated by the free DsRed. More strikingly, direct entry of VirE2 into the nucleus was visualized. To ensure that this observation was not a false co-localization due to an axial projection, a 3D opacity view of the nucleus was generated based on the same image data set; 3D rotation showed that the optical slices and VirE2-GFP$_{comp}$ signals were within the nucleus. This confirmed that the VirE2-GFP$_{comp}$ signa entered the nucleus. VirE2 moved at a speed of 1.1 μm/sec along the linear track, but it slowed down around the nucleus area. The average velocity was 0.434 μm/sec for this trafficking event observed. Generally speaking, VirE2 moved faster along a linear track although the velocities varied on different linear tracks; it moved slower along curved tracks.

VirE2 trafficking was sensitive to cytochalasin D and Brefeldin A

Next, in order to study the nature of cellular structure that facilitated the movement of *Agrobacterium*-delivered VirE2 inside plant cells. Transgenic plants (Nb308A) expressing GFP1-10 and free DsRed were treated with chemicals known to disrupt cellular structures. As shown in FIG. 1b-d, cytochalasin D (CytoD) and brefeldin A (BFA) severely affected the VirE2 trafficking, while colchicine (Colc) only exhibited a minor effect. The inventor monitored over 20 independent events of VirE2 movements for each treatment. The inventor found that CytoD and BFA treatment reduced the average velocities of VirE2 movement to less than 20%, while Colc treatment showed over 60% of the average velocity of the control (FIG. 1c).

CytoD is a potent inhibitor of actin polymerization, and BFA inhibits protein transport from endoplasmic reticulum (ER) to Golgi apparatus by dilating the ER_ENREF_13, while Colc inhibits microtubule polymerization. The inventor observed the effects of these inhibitors on the corresponding cellular structures in tobacco leaves under test conditions. Colc, BFA and CytoD indeed disrupted the microtubule, ER and actin structures, respectively. Therefore, the invention hypothesized that VirE2 trafficking was probably facilitated by ER/actin structures.

VirE2 movement was associated with endoplasmic reticulum.

In order to determine if VirE2 movement is associated with the endoplasmic reticulum, the present invention uses an ER-mCherry construct containing an ER targeting sequence at the N-terminus and the tetrapeptide retrieval signal HDEL at the C-terminus. Both GFP1-10 and ER-mCherry constructs were then introduced into a T-DNA harbored on a binary plasmid to generate pQH308ER. The plasmid was introduced into EHA105virE2::GFP11 expressing VirE2-GFP11 that is functional like wild-type VirE2.

The inventor infiltrated EHA105virE2::GFP11 (pQH308ER) into *N. benthamiana* leaves and then observed *Agrobacterium*-delivered VirE2-GFP$_{comp}$ signals. As shown in FIG. 2a, VirE2 aggregates appeared as dots or filaments inside tobacco cells. Both forms were co-localized with inter-connected ER tubules illustrated by ER-mCherry. The VirE2 filaments matched with the ER strands in an imperfect manner (lower panel). It is not clear whether the imperfect matching was real or due to the gap time required to detect the two different moving colors. Time-lapse imaging showed that VirE2 aggregates moved along the ER strands (FIG. 2b); the average velocity was 0.502 μm/sec during this linear movement, which is consistent with our earlier observations.

VirE2 exists on a cytosol side of the endoplasmic reticulum in the plant cells.

The inventor determined if VirE2 was present on the cytosolic or luminal side, as ER is an interconnected network of flattened, membrane-enclosed sacs or tubes known as cisternae and the ER membranes compartmentalize into ER lumen and cytosol. The inventor generated an ER-GFP1-10 construct containing an ER targeting sequence at the N-terminus of GFP1-10 and an ER retention signal HDEL at the C-terminus. The inventor also generated a two-tandem GFP11 (2×GFP11) and its ER-localizing construct (ER-2× GFP11) containing an ER targeting sequence at the N-terminus and an ER retention signal HDEL at the C-terminus.

These constructs were expressed in wild type N. benthamiana leaves by agro-infiltration. $GFP_{comp}$ signals were detected when ER-GFP-1-10 was co-expressed with ER-2× GFP11, but not with 2×GFP11 (FIG. 6a-b). This demonstrated that the ER-GFP1-10 construct was indeed localized inside ER lumen. EHA105virE2::GFP11 containing VirE2-GFP11 was infiltrated into N. benthamiana leaves which transiently expressed either GFP1-10 or ER-GFP1-10. As shown in FIG. 6c, Agrobacterium-delivered VirE2-GFP11 complemented GFP1-10, but not ER-GFP1-10. This demonstrated that Agrobacterium-delivered VirE2 was on the cytosolic side of ER after delivery into plant cytoplasm.

VirE2 moves along a F-actin filament.

Since the CytoD can stop the VirE2 movement (FIGS. 1b-d), and CytoD can be bound to the F-actin and prevent the monomer polymerization of F-actin, the present invention attempts to determine whether the VirE2 movement is associated with the F-actin filament.

Figure 3:
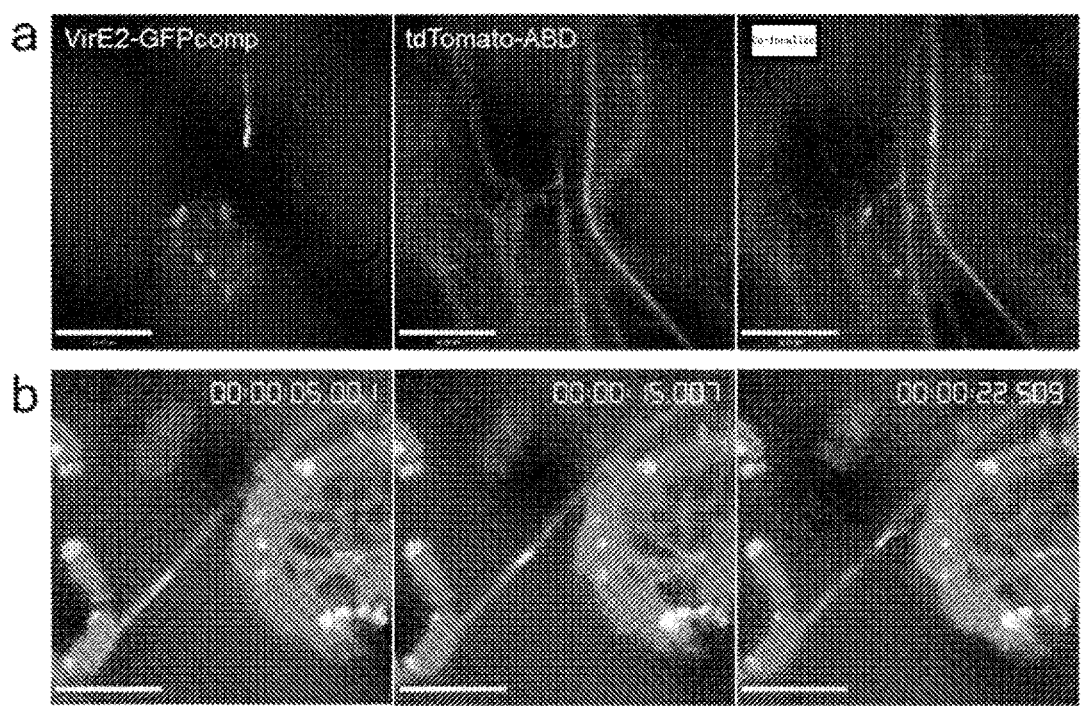
FIG. 3A is a sequence of images showing VirE2 aggregates co-localizing with F-actin filaments.
FIG. 3B is a sequence of time-lapse images of VirE2 aggregates trafficking on F-actin filaments.

In order to observe the F-actin and VirE2 simultaneously, the inventor injects and infiltrates the A. tumefaciens strain EHA105virE2::GFP11 into the tobacco plant (Nb307A) expressing the GFP1-10. Meanwhile, the strain carries a binary plasmid encoding a F-actin marker tdTomato-ABD2 for expression in the tobacco. As shown in FIG. 3, the VirE2-GFPcomp signal overlaps with a position of the F-actin filament. The time-lapse imaging shows that the VirE2 moves along the F-actin filament.

VirE2 Movement Depends on Mmyosin

Figure 4:
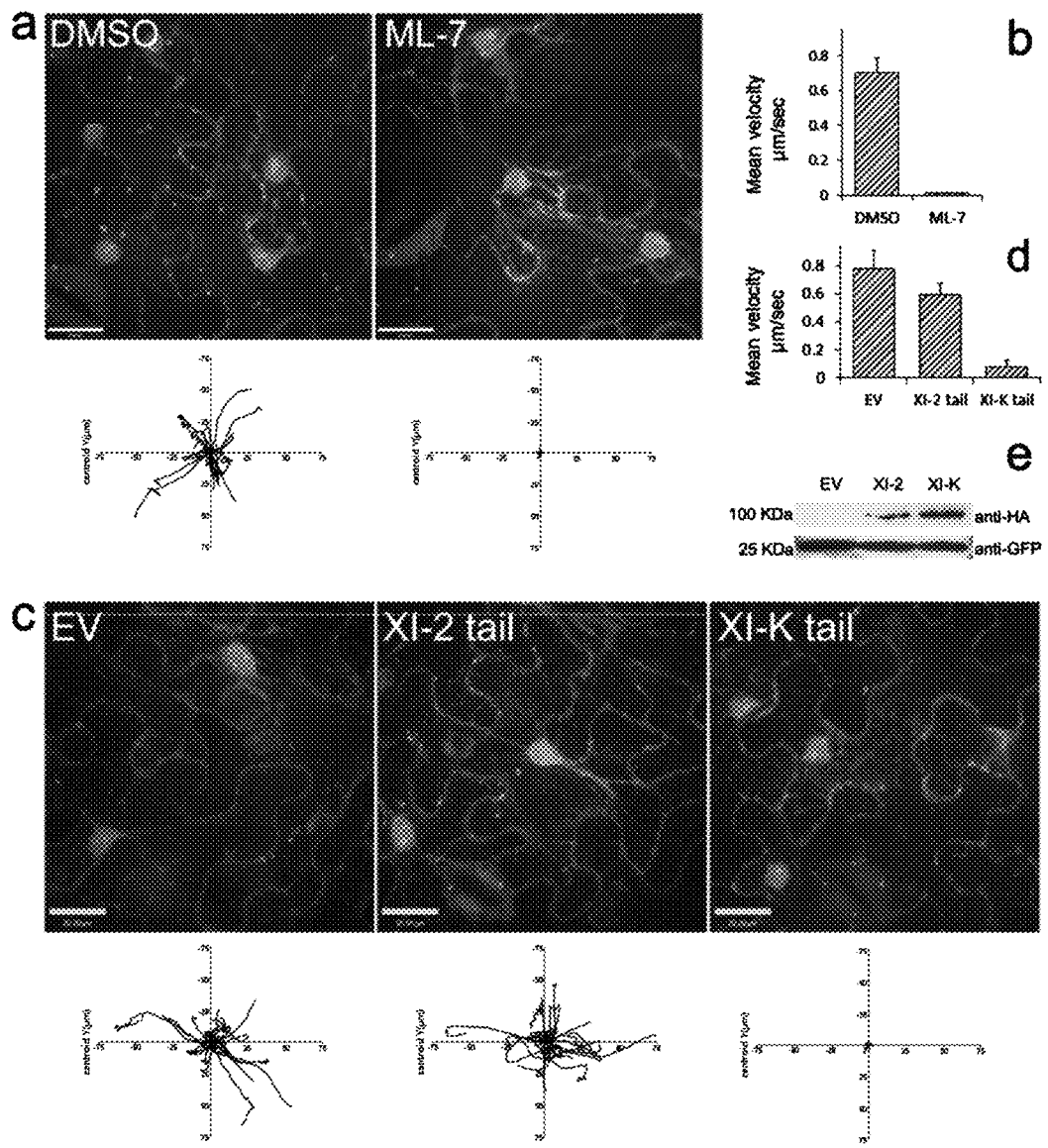
FIG. 4A is a sequence of images showing an effect of ML-7, a myosin light chain kinase inhibitor, on VirE2 trafficking.
FIG. 4B is a graph of mean velocity of the VirE2 aggregates after ML-7 treatment.
FIG. 4C is a sequence of images showing effects of myosin-tail overexpression on VirE2 trafficking.
FIG. 4D is a control experiment of mean velocity of VirE2 aggregate movement under overexpression of myosin tails.
FIG. 4E is a Western analysis of crude extracts from leaf samples agroinfiltrated with myosin-tail constructs.

Since the endoplasmic reticulum/F-actin/myosin can perform a three-way interaction, the inventor then decides to examine whether the myosin plays a role in the VirE2 movement in the plant cells. Firstly, the present invention uses a selective myosin light chain kinase inhibitor ML-7 to inhibit an activity of a plant myosin. As shown in FIG. 4, ML-7 treatment obviously stops the VirE2 movement. Compared with a control group, an average rate of the movement of the VirE2 decreases by 95%.

Next, the inventor uses a dominant-negative approach to identify the specific myosin responsible for VirE2 movement. Several dominant negative mutants of plant myosin genes were overexpressed during Agrobacterium-mediated delivery of VirE2, since headless myosin tails could interrupt myosin activity in a dominant negative manner. A. tumefaciens cells containing T-DNA harboring the tail constructs were co-infiltrated with EHA105virE2::GFP11 into tobacco plants (Nb308A) expressing GFP1-10 and the free DsRed; the myosin tail expression would take place later than VirE2 delivery so that the myosin mutant constructs would not affect the VirE2 delivery. Among the myosin mutants tested, only XI-K tail remarkably arrested the VirE2 trafficking (FIG. 4c and FIG. 7c); the average velocity was reduced to 10% as compared to the control (FIG. 4d). In contrast, overexpression of XI-2 and other myosin tails exhibited only a minor or insignificant effect (FIG. 4c and FIG. 7c). These data suggest that myosins provide the driving force for VirE2 movement and myosin XI-K was the most important contributor.

It is of particular interest to determine if the VirE2 movement inside the cell is dependent upon the NLS. Since a mutation at NLS1 of VirE2 rendered VirE2 non-functional, any ER marker construct would not be expressed transiently using the VirE2 NLS1 mutant strain. However, introducing a second strain to deliver functional VirE2 would inevitably generate chimeric VirE2 aggregates which could interfere with the behavior of VirE2ΔNLS1. Therefore, the present invention establishes transgenic tobacco Nb308ER, which constitutively express GFP1-10 and ER-mCherry.

Figure 8:
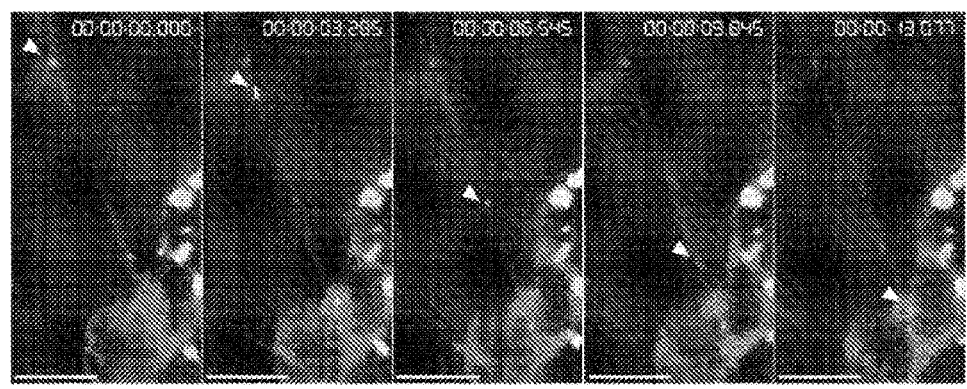
FIG. 8 illustrates a time-lapse imaging of a NLS1-mutant VirE2 moving on an endoplasmic reticulum filament.

EHA105virE2ΔNLS1::GFP11 was infiltrated into the epidermal cells of Nb308ER As shown in FIG. 8, VirE2ΔNLS1 was co-localized with ER strands and moved along the ER strands. This demonstrated that VirE2 movement inside the cytoplasm was independent of NLS, although NLS is required for nuclear targeting.

Myosin XI-K is required for A. tumefaciens-mediated transformation.

Figure 9:
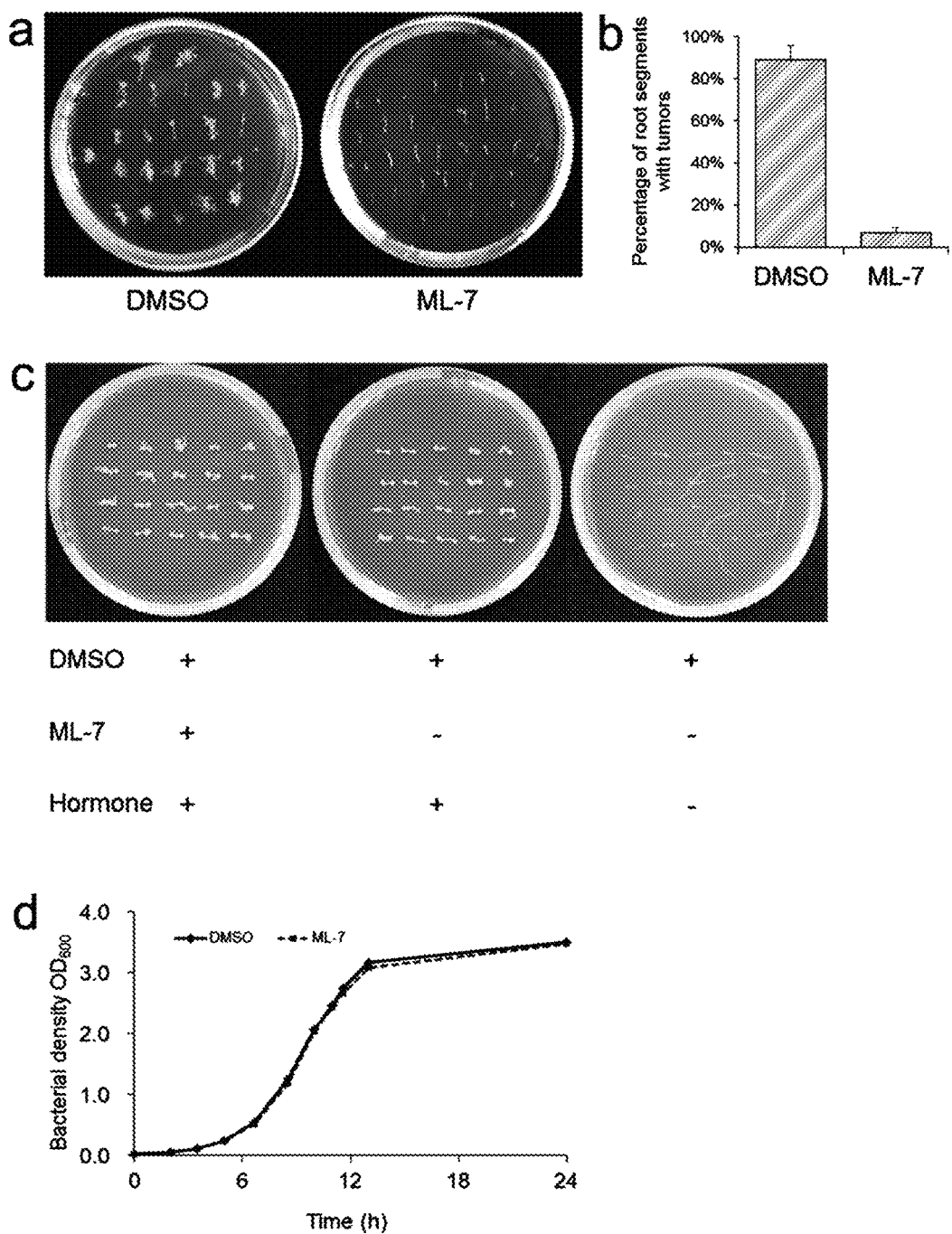
FIG. 9A is an image tumors formed with or without ML-7 treatment in which ML-7 was added (10 µM) into the col-cultivation mixture and then washed off when the root segments were transferred onto new plates for tumor formation.
FIG. 9B is a graph showing tumorigenesis efficiency as determined by percentage of root segments with tumors.
FIG. 9C is a series of images showing the effect of ML-7 on root segment viability.
FIG. 9D is a graph showing the effect of ML-7 on *Agrobacterium* viability.

The inventor wants to determine if the VirE2 movement observed during our studies is directly relevant to Agrobacterium-mediated transformation. The present invention tested the effect of a selective myosin light chain kinase inhibitor ML-7 on Arabidopsis root transformation. Root segments were inoculated with a tumor inducing strain A348 in the presence of 10 μM ML-7. As shown in FIG. 9, ML-7 significantly reduced the transformation efficiency. The present invention tested the toxicity of ML-7 on either the root or Agrobacterium growth at 10 μM ML-7. The root segments were exposed to 10 μM of ML-7 for 2 days, which was the time span for the bacterium-Arabidopsis co-cultivation. As shown in FIG. 9c, ML-7 did not affect the growth of root segments in the presence of hormones (auxin and cytokinin); ML-7 did not inhibit Agrobacterium growth either (FIG. S5d). These suggest that inhibition of myosin activity could reduce the transformation efficiency.

Figure 10:
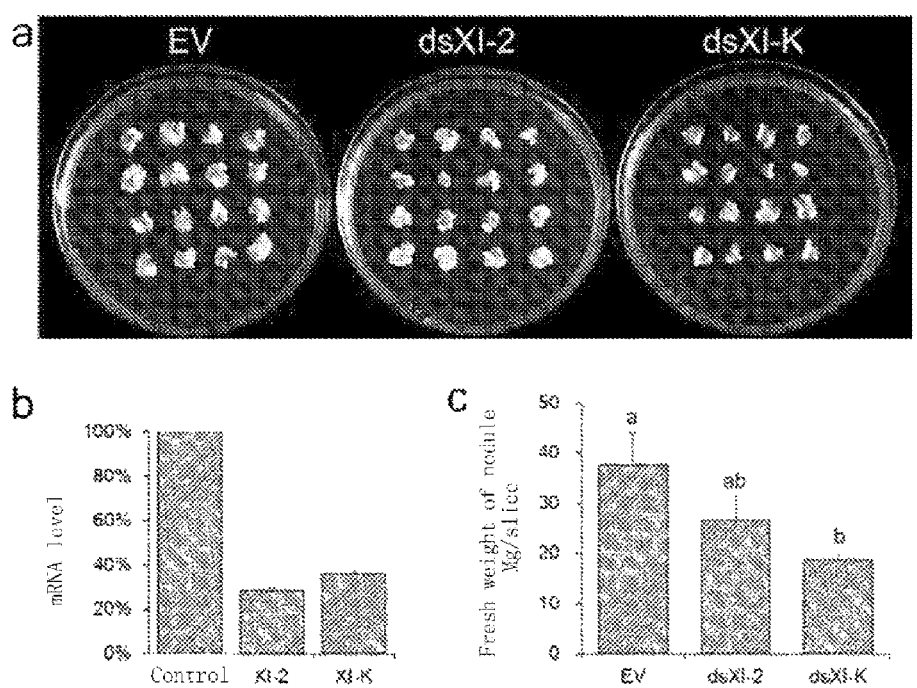
FIG. 10A is a series of images that illustrates the effects of RNAi silencing of XI-2 and XI-K on tumor formation.
FIG. 10B is a graph that illustrates the effects of RNAi silencing of XI-2 and XI-K on tumor formation.
FIG. 10C effects of RNAi silencing of XI-2 and XI-K on tumor formation.

To confirm the specific effect of myosin inhibition on transformation, the inventor uses RNAi constructs containing partial sequence of XI-2 and XI-K (48) to silence the corresponding genes. The RNAi constructs used for the studies could generate specific effects but not off-target effects. As shown in FIG. 10, silencing of XI-K evidently attenuated tumor formation. The data clearly indicated that XI-K affected the VirE2 movement and consequently affected Agrobacterium-mediated transformation.

Toxicity Determination of Drug

Figure 11:
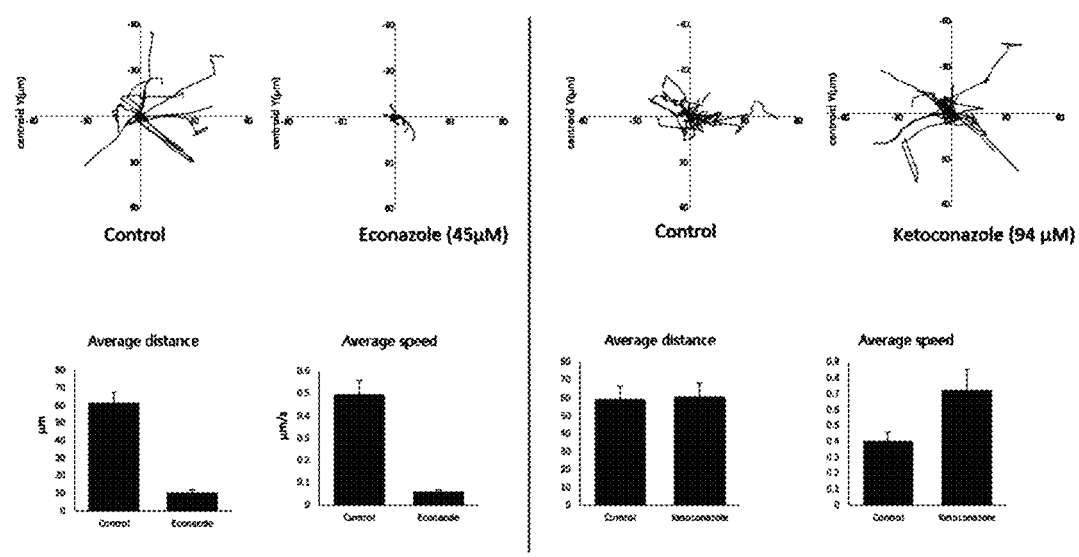
FIG. 11 illustrates an effect of a drug on the VirE2 movement.

The present invention tests several drugs and finds that drug Ketoconazole on the market does not affect a real-time movement process of a protein VirE2-GFP and is considered to be less toxic; while Econazole significantly affects the real-time movement process of the protein VirE2-GFP and is considered to be highly toxic (FIG. 11).

Discussion

A. tumefaciens has an exceptional ability to transform a wide range of host plants in nature and various recipient cells under laboratory conditions. In addition, the bacterium can achieve a high efficiency of transformation up to 100% of the plant cells in contact with the bacteria. The high efficiency enabled us to dissect the movement of Agrobacterium-delivered VirE2 inside plant cells. As the present invention shows here, the bacterium hijacks conserved host network to move virulence factor VirE2 towards the nucleus. This might be important for Agrobacterium to achieve both a wide host range and a high efficiency.

In order to transform plant cells, Agrobacterium must be able to deliver its virulence factors into host cells efficiently. These exogenous factors must be able to move towards appropriate locations to exercise their functions inside host cells. It is indeed a challenge to study how these proteins are trafficked through the cytoplasm and reach the nucleus, as this is a complex process and any disturbance to the process in an in vitro system might generate artefacts.

The present invention adopted a split-GFP approach to visualize VirE2 in a natural setting, which made it possible to monitor intracellular trafficking of the virulence effector VirE2 in real time. The studies showed that *Agrobacterium*-delivered VirE2 were trafficked via endoplasmic reticulum (ER) and F-actin network; this process was powered by myosin XI-K in particular. It is known that ER, actin filaments and myosins can interact with each other to form a network. The data of present invention showed that exogenously produced and then delivered VirE2 protein complex could use endogenous host ER/actin network for its trafficking inside host cells.

VirE2 is critical for the fate of T-DNA in many ways. Therefore, it is of particular significance to study how VirE2 is trafficked through the cytoplasm and reaches the nucleus. VirE2 contains two bipartite NLS signals, which are present on the exterior side of the solenoidal structure. This kind of structural arrangement may make the NLS signals available to interact with other host factors for VirE2 trafficking.

Indeed, VirE2 was shown to interact with *Arabidopsis* importin α isoform IMPa-4 when both proteins were over-expressed; VirE2 localized in the plant nucleus. When the NLS of VirE2 was mutated to be recognizable in animal cells, the "animalized" VirE2 was found to migrate along microtubules in cell-free *Xenopus* oocyte extracts, and dynein motors were important for this migration. However, no plant dyneins have been found. It remains unknown whether VirE2 moves along microtubules in plant cells. The "animalized" VirE2 trafficking in an animal cell context therefore might not necessarily represent the mode of VirE2 trafficking inside plant cells. In fact, disruption of microtubules by colchicine did not affect the VirE2 trafficking significantly (FIG. 1*d*). These suggest that VirE2 uses a trafficking system other than microtubules for its trafficking inside plant cells.

In an in vivo trafficking system, there was no disturbance to the cellular infrastructures; the studies revealed myosin-dependent trafficking of VirE2 in planta in a natural setting. Presumably, VirE2-associated T-complex may also use the same trafficking mode, as VirE2 can coat T-complex on the surface. Therefore, this study may provide a plausible explanation to the tremendous difference in transformation efficiency between yeast and plant recipients (0.2% in *S. cerevisiae* vs 100.0% in *N. benthamiana*), while the efficiency of protein delivery is comparable (50.9% in *S. cerevisiae* vs 100.0% in *N benthamiana*). VirE2 trafficking may require plant-specific myosin XI family, XI-K in particular. The budding yeast *Sacchromyces cerevisiae*, on the other hand, lacks myosin XI-K. This would render VirE2 immobile in the yeast cells; thus the transformation efficiency is strongly attenuated as reported previously.

Myosins are the important motor proteins that move on actin filaments in eukaryotic cells. In plant cells, myosins can be categorized into three main classes, myosin VIII, XI and XIII Myosin XI family members are evolutionarily related to the animal myosin V family, and are involved in the cytoplasmic streaming, ER motility, and trafficking of organelles and vesicles. The myosin XI family comprises fast motor members that can traffic at several micrometers per second, which surpasses its myosin V family counterparts by over ten folds. Despite the conformational similarity with myosin V, myosin XI has a plant specific binding mechanism and thus recognizes cargos that are distinct from myosin V. Our studies demonstrated that myosin XI-K played a much more critical role in VirE2 trafficking than XI-2. Both XI-K and XI-2 are highly expressed inside plant cells. However, myosin XI-K is the primary contributor to ER streaming as compared to XI-2.

The present invention assumes that that *Agrobacterium* has evolved to enable VirE2 to take the free-ride of a fundamental process: ER streaming, which is part of cytoplasmic streaming. *Agrobacterium*-delivered VirE2 was associated with ER (FIG. 2*b*), presumably because the high affinity of VirE2 to membranes enabled VirE2 to associate with ER, which has extensive membrane structures. Of course, it is also possible that an unknown factor(s) is responsible for VirE2-ER association. VirE2-associated ER is then driven primarily by ER-associated myosin XI-K. Myosin-associated ER can move along actin filaments. Therefore, *Agrobacterium*-delivered VirE2 is trafficked through plant cells via myosin-powered ER/actin network, because of the dynamic three-way interactions between ER, F-action and myosin. At this stage, it is not clear which part of VirE2 is required for VirE2 movement. This remains to be solved in the future.

The endoplasmic reticulum stretches through the entire cytoplasm and continues with outer membrane of nucleus, which would provide VirE2 a convenient path to reach the nucleus. Cytosolic facing of VirE2 on the ER would presumably make the opening of nuclear pore complex accessible for nuclear import of VirE2 that contains the NLS. Moreover, the association of VirE2 with ER also suggests that VirE2 may interact with other factors during the trafficking processes. Indeed, a SNARE-like protein was found to have a strong interaction with VirE2. This suggests that vesicular budding or fusion processes may be involved in VirE2 trafficking inside the cytoplasm. Currently, it is still not clear whether any of other bacterial virulence proteins delivered by *Agrobacterium* would be trafficked along with VirE2. It remains to be established how other bacterial virulence proteins are trafficked inside host cells upon the delivery. These issues should be examined in the future studies, which could lead to important findings that may provide new insight into the transformation process.

Optimum Mode for Implementing Invention

The present invention is further described by specific embodiments with reference to the drawings, but it shall be understood that these embodiments are only for the object of more detailed description and shall not be construed as limiting the present invention in any form.

This section gives a general description to the materials and experimental methods used in experiments of the present invention. Although many materials and operation methods used to achieve the objective of the present invention are well known in the art, the present invention is still described here in as much detail as possible. It is clear to those skilled in the art that the materials and operation methods used in the present invention are well known in the art in the context, unless otherwise specified.

First of all, the materials and experimental methods used in various embodiment are uniformly described as follows.

Strains, Plasmids, Primers and Growth Conditions

The strains and the plasmids used in the experiment are listed in Table 1.

TABLE 1

Strains and Plasmids Used in Experiment

| Strain and plasmid | Correlation characteristic |
| --- | --- |
| *A. tumefaciens* | |
| EHA105 | A C58 strain contains a pTiBo542 plasmid, contains a vir gene, but does not contain a T-DNA |
| EHA105virE2::GFP11 | An EHA105 derivative strain, comprising 162 bp after ATG with a GFP11 coding sequence inserted into a virE2 gene on a pTiBo542 |
| EHA105virE2::GFP11nlsl | An EHA105virE2::GFP11 derivative strain, the first nuclear targeting signal sequence is replaced with alanine from 221KLR . . . KYGRR237 |
| A348 | A136 (pTiA6NC) (Octopine-type) |
| Plasmid | |
| pQH308A | The GFP1-10 coding sequence is inserted into a pDs-Lox and replaces a Bar in the pDs-Lox. An obtained Pmas:GFP1-10:Tnos component is amplified by a PCR and inserted into a ClaI-HindIII site on a pBI121; a DsRed ORF is inserted into an XbaI-BamHI site on the pBI121 and under a 35S promoter. |
| pER-rk | A binary plasmid encodes a mCherry sequence located on an ER. |
| pQH308ER | An ER-mCherry sequence cloned from a pER-rk is replaced with a DsRed coding sequence on a pQH308A. |
| pQH307A | The DsRed coding sequence on the pQH308A is deleted. |
| pCB302 | Mini binary plasmid with the 35S promoter |
| pCB302-XIK-IQC | A pCB302 plasmid expresses a fragment of a tail end of a myosin XI-K from Ala731. |
| pCB302-XI2-IQC | pCB302 plasmid expresses a fragment of a tail end of a myosin XI-2 from Val735. |
| pCB302-XIF-IQC | pCB302 plasmid expresses a fragment of a tail end of a myosin XI-F from Ile740. |
| pCB302-VIII1-IQC | pCB302 plasmid expresses a fragment of a tail end of a myosin VIII1 from Thr827. |
| pCB302-VIII2-IQC | pCB302 plasmid expresses a fragment of a tail end of a myosin VIII2 from Glu864. |
| pCB302-VIIIB-IQC | pCB302 plasmid expresses a fragment of a tail end of a myosin VIIIB from Val831. |
| pCB302-dsXIK | pCB302 plasmid expresses an RNAi component, covering a nucleotide sequence interval of open reading frames 3,153-3,357 of the myosin XI-K |
| pCB302-dsXI2 | pCB302 plasmid expresses the RNAi component, covering a nucleotide sequence interval of open reading frames 3,146-3,357 of the myosin XI-2 |
| pB5tdGW-ABD2 | binary plasmid encodes a tdTomato-fusion actin. |
| pH7WGR2-RFP-MBD | The binary plasmid encodes an RFP-fusion microtubule binding domain. |
| pBI121 | The binary plasmid has the 35S promoter and a Gus-A coding sequence. |
| pQH121 | The Gus-A coding sequence in the pBI121 is replaced by a multiple cloning site. |
| pQH121-ER-GFP1-10 | A pQH121 encodes the GFP1-10 sequence, and is fused with an ER localization signal at the N end and is fused with an HDEL ER-reservation signal at the C terminus. |
| pQH121-2×GFP11 | The pQH121 encodes two GFP11 in series. |
| pQH121-ER-2×GFP11 | The pQH121 encodes two GFP11 in series, and is fused with the ER localization signal at the N end and is fused with the HDEL ER-reservation signal at the C terminus. |

*A. tumefaciens* (*Agrobacterium tumefaciens*) grows in a MG/L medium and an induction medium (IBPO4) at 28° C. An *Escherichia coli* (*E. coli*) DH5α strain is used for plasmid construction and grows in a LB medium at 37° C.

Plasmid construction and production of transgenic tobacco plant (*N. benthamiana*)

Binary plasmids harboring a T-DNA region that encodes either a GFP1-10 expression cassette or a GFP1-10 and ER-mCherry dual cassettes were constructed and then used to generate transgenic *N. benthamiana* lines. Plasmid pQH308A(28) was digested with XbaI and SacI to remove the coding sequence of DsRed. The linearized plasmid was then re-ligated after the overhanging sticky ends were blunted by Klenow fragment, resulting in pQH307A. The coding sequence of ER-mCherry from pER-rk (44) was cloned into the XbaI-SacI site of pQH308A to replace DsRed, resulting in pQH308ER.

*Agrobacterium*-mediated transformation of *N. benthamiana* plants was performed using leaf sections. Transgenic calli were generated on Murashige and Skoog (MS) media

(64) supplemented with 100 mg L$^{-1}$ kanamycin, 2 mg L$^{-1}$ 6-BA and 0.2 mg L$^{-1}$ NAA. Transgenic tobacco plantlets were obtained by transferring the calli with shoots into ½ MS plates supplemented with 0.1 mg L$^{-1}$ IBA. Transgenic lines were then named as Nb307A and Nb308ER to reflect the corresponding binary plasmids pQH307A and pQH308ER.

Virulence Assays

Arabidopsis thaliana seeds were surface-sterilized with 0.5% NaClO solution and placed onto solidified ½×MS medium supplemented with 1% sucrose and 0.5 g L$^{-1}$ MES, pH 5.8. The plates were then incubated under a 16 hour photoperiod at 25° C. for 10 to 12 days. Roots from individual seedlings were cut into 3-5 mm segments and re-suspended in 1 ml fresh ½×MS medium containing A. tumefaciens cells at a concentration of 5×10$^8$ cell/ml unless specified otherwise. The mixtures were spread onto a solidified ½×MS plate and subsequently incubated at 25° C. for 2 days. The root segments were aligned onto ½×MS medium plates containing 100 mL$^{-1}$ cefotaxime and kept at 25° C. for 4 weeks before photographing.

Leaves of N. benthamiana were surface sterilized with 0.5% NaClO and punctured into discs. The leaf discs were resuspended into ½×MS medium containing A. tumefaciens cells at a concentration of 1×10$^8$ cell/ml unless specified otherwise. The leaf discs were aligned onto a ½×MS plate and subsequently incubated at 25° C. for 2 days. The leaf discs were then transferred onto another ½×MS plate supplemented with 100 µg mL$^{-1}$ cefotaxime and kept at 25° C. for 2 weeks before imaging.

Agroinfiltration

To visualize Agrobacterium-delivered VirE2, agroinfiltration was performed as described previously. Briefly, the bacteria were grown overnight; the cultures were diluted 50 times in MG/L and grown for 6 h. The bacteria were collected and re-suspended in infiltration buffer (10 mM MgCl$_2$, 10 mM MES, pH5.5) to OD$_{600}$=1.0. The bacterial suspension was infiltrated using a syringe to the underside of fully expended N. benthamiana leaves. The infiltrated plant was placed at 22° C. in a photoperiod of 16 h light/8 h dark. In order to observe a real-time effect of a compound or a drug on cells in real time, the inventor injected and infiltrated the compound or the drug into a leaf injected and infiltrated with A. tumefaciens EHA105virE2::GFP11 cell at an appropriate concentration, and observed with a UPL-SAPO×60 N.A. 1.20 water immersion lens under a confocal microscope after six hours.

Detection of mRNA by qRT-PCR Method

To quantify the mRNA level in RNAi-silenced plants, total RNA from plants for each treatment was extracted and reverse transcribed by iScript cDNA synthesis kit (Bio-Rad). Quantitative RT-PCR was performed in triplicates with KAPA SYBRs on CFX384 Real-Time PCR system (Bio-Rad) by using the actin gene as an internal control (5'-CTTGAAACAGCAAAGACCAGC-3' and 5'-GGAATCTCTCAGCACCAATGG-3'). Gene specific primers for qRT-PCR are as follows: 5'-TCGTTTCGGTAAGTTTGTGG-3' and 5'-CATTGCCCTTCTTGTAGCC-3' for N. benthamiana myosin XI-2 gene (accession number DQ875135), 5'-GAATCAGT-GAGGAAGAGCAGG-3' and 5'-CCGTCATATTGAGAT-GAAATCG-3' for N. benthamiana myosin XI-K gene (accession number DQ875137).

Confocal Microscopy

A PerkinElmer UltraView Vox Spinning Disk system with EM-CCD cameras was used for confocal microscopy. To observe leaf epidermis, agroinfiltrated leaf tissues were detached from N. benthamiana plants and put in 2% low-melting agarose gel on a glass slide with a coverslip. All images were taken in multiple focal planes (Z-stacks), and were processed to show the extended focus image or 3D opacity view by Volocity® 3D Image Analysis Software 6.2.1.

Embodiment 1: Agrobacterium-Delivered VirE2 Trafficking on a Cellular Structure and Entering the Nucleus FIG. 1 illustrated Agrobacterium-delivered VirE2 trafficking on a cellular structure and entering the nucleus. A. tumefaciens EHA105virE2::GFP11 cells were infiltrated into transgenic N. benthamiana (Nb308A) leaves expressing both GFP1-10 and DsRed. The leaf epidermal cells were observed at 2 d post agroinfiltration under confocal microscope with UPLSAPO×60 N.A. 1.20 water immersion objective. Red, free DsRed; Green, VirE2-GFP$_{comp}$. (a) Time-lapse images of VirE2 aggregates trafficking along a linear cellular structure and entering the nucleus. Relative time is shown at the top right. Scale bar represents 20 µm. (b) Effects of chemical treatments on VirE2 trafficking. Chemicals were infiltrated into leaf samples 6 h before observation. Control, 0.5% DMSO. Colc, colchicine 500 CytoD, cytochalasin D 20 µM. BFA, brefeldin A 100 µg/mL. Scale bar represents 20 µm. (c) Mean velocities of VirE2 aggregate movement after chemical treatments. Data analyzed with ANOVA and Tukey test, p<0.05. (d) Movement tracking of 20 individual VirE2 aggregates plotted to a common origin for each treatment.

Figure 2:
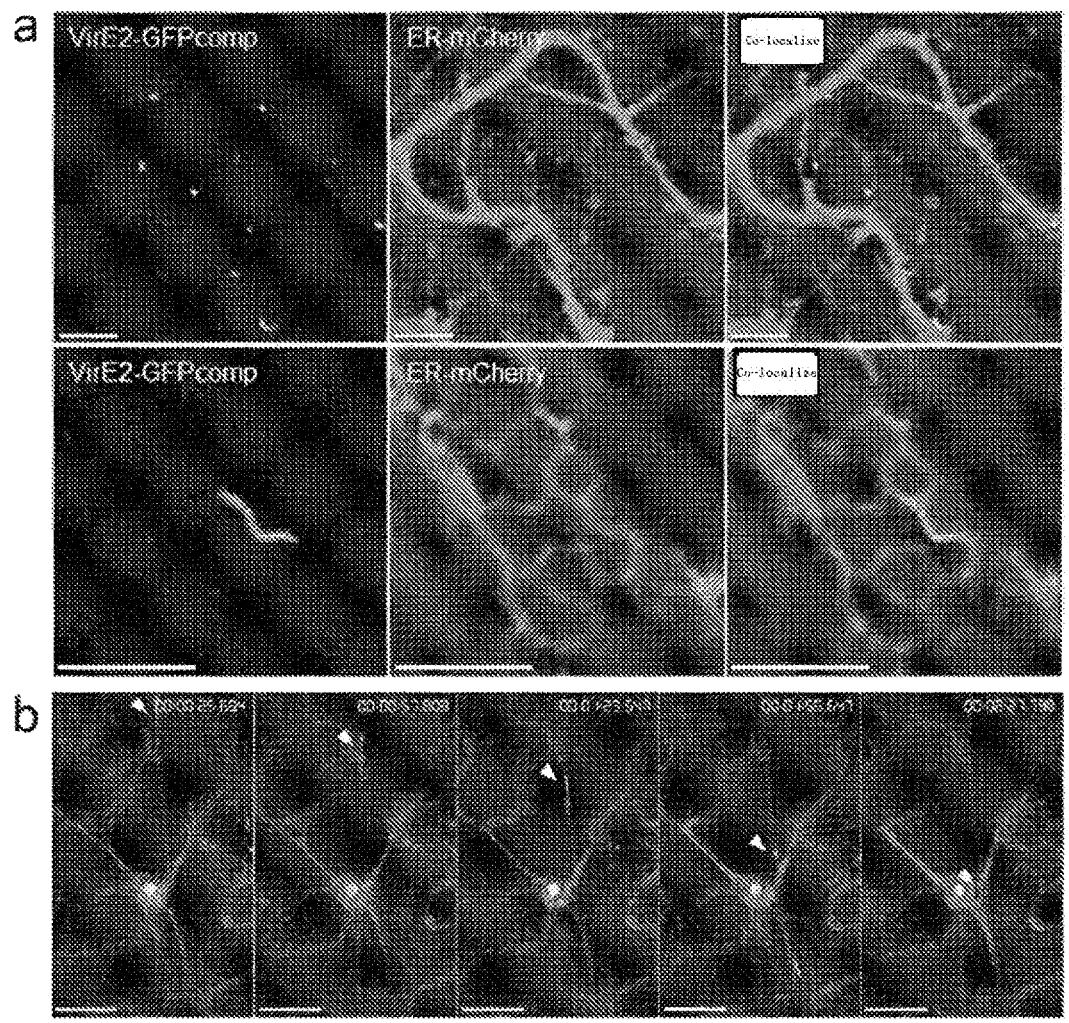
FIG. 2A is a sequence of images showing VirE2 aggregates co-localizing with inter-connected ER tubules as dots or filaments.
FIG. 2B is a time-lapse sequence of images of VirE2 aggregates trafficking on an ER strand.

Embodiment 2: Agrobacterium-Delivered VirE2 Co-Localizing with and Trafficking on the ER Network FIG. 2 illustrated Agrobacterium-delivered VirE2 co-localizing with and trafficking on the ER network. A. tumefaciens EHA105virE2::GFP11 cells harboring a binary plasmid pQH308ER, which encodes an ER-mCherry marker driven by 35S promoter and GFP1-10 driven by mas promoter, were infiltrated into wild type N. benthamiana leaves. The leaf epidermal cells were observed at 2 d post agroinfiltration under confocal microscope with UPLSAPO×60 N.A. 1.20 water immersion objective. Red, ER-mCherry; Green, VirE2-GFP$_{comp}$. (a) VirE2 aggregates co-localizing with inter-connected ER tubules. Scale bar represents 10 µm. (b) Time-lapse images of VirE2 aggregates trafficking on an ER strand. Relative time is shown at the top right. Scale bar represents 20 µm.

Embodiment 3: Agrobacterium-Delivered VirE2 Co-Localizing and Trafficking on F-actin Filaments FIG. 3 illustrated that Agrobacterium-delivered VirE2 co-localizing and trafficking on F-actin filaments. A. tumefaciens EHA105virE2::GFP11 cells bearing a binary plasmid pB5tdGW-ABD2, which encodes an actin marker tdTomato-ABD2 driven by 35S promoter, were infiltrated into transgenic *N. benthamiana* Nb307A which constitutively expressing GFP1-10. The leaf epidermal cells were observed at 2 d post agroinfiltration under confocal microscope with UPLSAPO×60 N.A. 1.20 water immersion objective. Red, F-actin; Green, VirE2-GFP$_{comp}$. (a) VirE2 aggregates co-localizing with F-actin filaments. Scale bar represents 20 μm. (b) Time-lapse images of VirE2 aggregates trafficking on F-actin filaments. Relative time is shown at top right. Scale bar represents 10 μm.

Embodiment 4: Effects of ML-7 and Myosin-Tail Overexpression on VirE2 Trafficking FIG. 4 illustrated effects of ML-7 and myosin-tail overexpression on VirE2 trafficking. (a) Effect of ML-7, a myosin light chain kinase inhibitor, on VirE2 trafficking. *A. tumefaciens* EHA105virE2::GFP11 cells were infiltrated into transgenic *N. benthamiana* (Nb308A) leaves expressing both GFP1-10 and DsRed. The leaves were infiltrated with 100 μM ML-7 or 1% DMSO as control 4 h before imaging. The leaf epidermal cells were observed at 2 d post agroinfiltration under confocal microscope with UPLSAPO×60 N.A. 1.20 water immersion objective. Red, free DsRed; Green, VirE2-GFP$_{comp}$. The movement tracking of 20 individual VirE2 aggregates plotted to a common origin is shown below the figure. Scale bar represents 20 μm. (b) Mean velocity of the VirE2 aggregates after ML-7 treatment. (c) Effects of myosin-tail overexpression on VirE2 trafficking. *A. tumefaciens* EHA105virE2::GFP11 cells harboring a binary plasmid which encodes a tail fragment of respective myosins downstream of 35S promoter were infiltrated into transgenic *N. benthamiana* (Nb308A) leaves expressing both GFP1-10 and DsRed. The leaf epidermal cells were observed at 2 d post agroinfiltration under confocal microscope with UPLSAPO×60 N.A. 1.20 water immersion objective. Red, free DsRed; Green, VirE2-GFP$_{comp}$. The movement tracking of 20 individual VirE2 aggregates plotted to a common origin is shown below the figure. Scale bar represents 20 μm. (d) Mean velocity of VirE2 aggregate movement under overexpression of myosin tails. EV, empty vector control. (e) Western analysis of crude extracts from leaf samples agroinfiltrated with myosin-tail constructs. EV, empty vector control. Myosin tails were HA tagged. GFP1-10 was detected to assess the amount of sample loaded, as shown in the lower panel.

Figure 5:
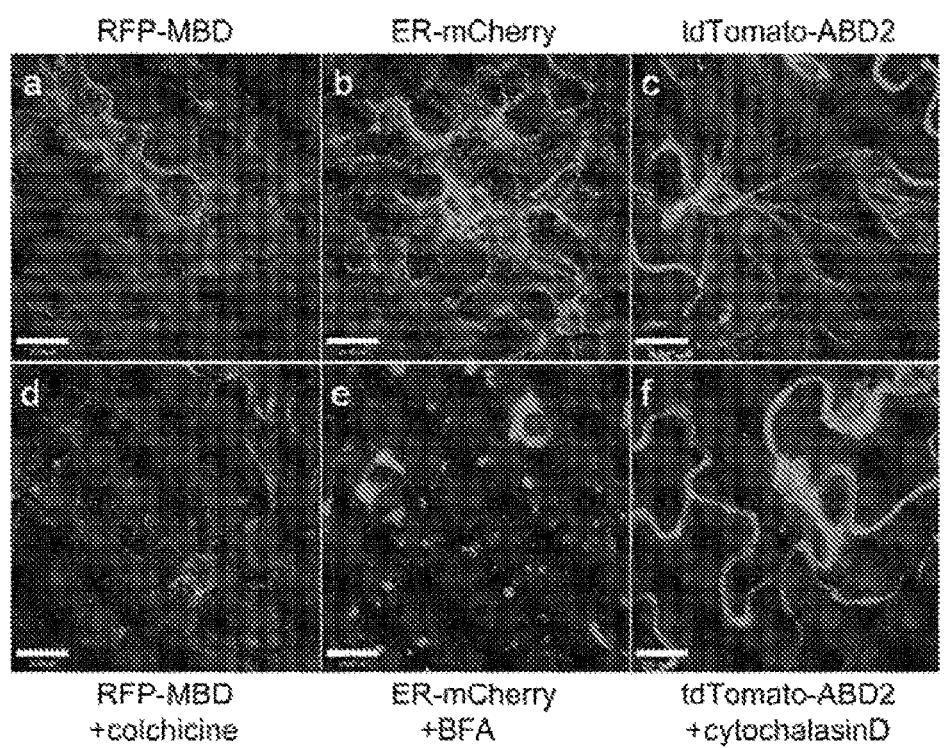
FIG. 5A is an image showing the effects of RFP on MBD (Microtubule Binding Domain)
FIG. 5B is an image showing the effects of ER on mCherry.
FIG. 5C is an image showing the effects of tdTomato on ABD2 where ABD is Actin Binding Domain.
FIG. 5D is an image showing the effects of RFP on MBD in which leaf samples were treated with 500 µM colchicine at 6 h before imaging.
FIG. 5E is an image showing the effects of ER on mCherry in which leaf samples were treated with 100 mM BFA at 6 h before imaging.
FIG. 5F is an image showing the effects of (f) tdTomato on ABD in which leaf samples were treated with 20 µM cytochalasin D at 6 h before imaging.

Embodiment 5: FIG. 5 Illustrated Effects of Chemicalson Respective Cell Structure FIG. 5 illustrated effects of chemicals on respective cellular structures. Wild type *N. benthamiana* leaves were agroinfiltrated with binary plasmids encoding different fluorescent markers. The epidermal cells were examined at 2 d post agroinfiltration under confocal microscope with Olympus UPLSAPO 60×N.A. 1.20 water immersion objective. Upper panels a-c: leaf samples expressing subcellular markers. Lower panels d-f: leaf samples expressing subcellular markers were treated with chemicals. (a) RFP-MBD. MBD, Microtubule Binding Domain. (b) ER-mCherry. (c) tdTomato-ABD2. ABD, Actin Binding Domain. (d) RFP-MBD. Leaf samples were treated with 500 μM colchicine at 6 h before imaging. (e) ER-mCherry. Leaf samples were treated with 100 μg/mL BFA at 6 h before imaging. (f) tdTomato-ABD. Leaf samples were treated with 20 μM cytochalasin D at 6 h before imaging. Scale bar represents 20 μm.

Figure 6:
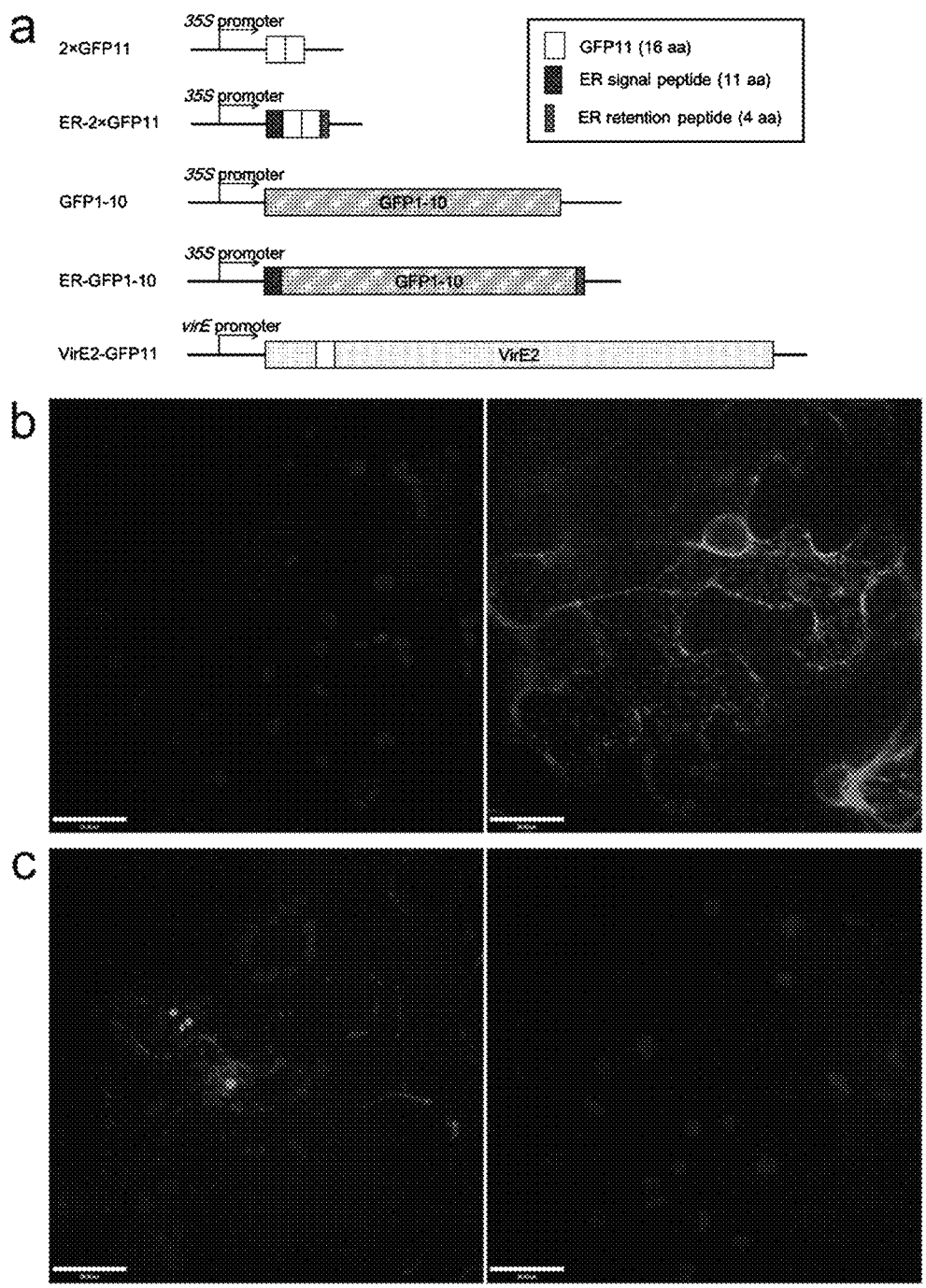
FIG. 6A is a diagram illustrating that *Agrobacterium*-delivered VirE2 is present on the cytosolic side of ER, in particular, the gene constructs introduced into tobacco cells.
FIG. 6B shows side by side images of the co-expression of 2·GFP11 and ER-GFP1-10 on the left and co-expression of ER-2·GFP11 and ER-GFP1-10 on the right.
FIG. 6C shows side-by-side images of the agroinfiltration of EHA105virE2::GFP11 harboring a binary plasmid encoding GFP1-10 on the left and the agroinfiltration of EHA105virE2::GFP11 harboring a binary plasmid encoding ER-GFP1-10 on the right.

Embodiment 6: FIG. 6 Illustrated that *Agrobacterium*-Delivered VirE2 Present on the Cytosolic Side of ER Endoplasmic Reticulum FIG. 6 illustrated that *Agrobacterium*-delivered VirE2 is present on the cytosolic side of ER. Wild type *N. benthamiana* leaves were agroinfiltrated with binary plasmids encoding GFP1-10 or GFP11 with or without ER targeting signals. The epidermal cells were examined at 2 d post agroinfiltration under confocal microscope with Olympus UPLSAPO 60×N.A. 1.20 water immersion objective. (a) The gene constructs introduced into tobacco cells. (b) Left: co-expression of 2×GFP11 and ER-GFP1-10; right: co-expression of ER-2×GFP11 and ER-GFP1-10. (c) Left: agroinfiltration of EHA105virE2::GFP11 harboring a binary plasmid encoding GFP1-10. Right: agroinfiltration of EHA105virE2::GFP11 harboring a binary plasmid encoding ER-GFP1-10. Scale bar represents 20 μm.

Figure 7:
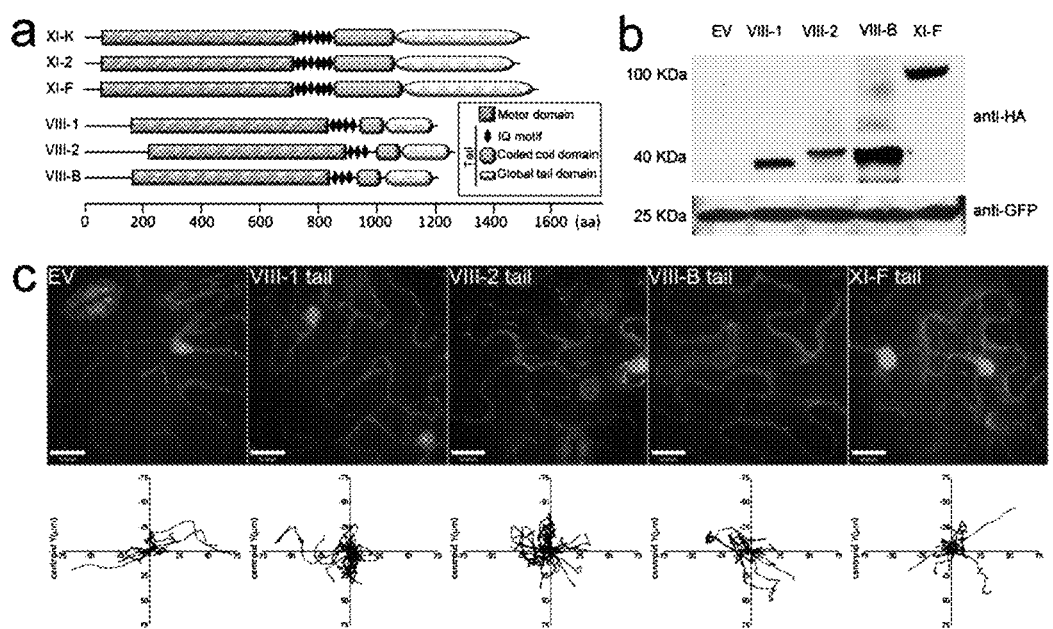
FIG. 7A is a schematic presentation of different myosin-tail constructs that were introduced into tobacco cells to illustrate the effects of myosin-tail overexpressions on VirE2 trafficking.
FIG. 7B is a Western analysis of leaf samples agroinfiltrated with myosin tail constructs in which: EV, is empty vector control, Myosin tails were HA tagged, and GFP1-10 was detected to assess the amount of sample loaded, as shown in the lower panel.
FIG. 7C is a series of images of the effects of myosin tail overexpressions on VirE2 trafficking in which Z-slices were captured with 0.5 µm step and showing extended focus image with a scale bar that represents 20 µm and the images are superimposed over depictions of corresponding movement tracking of 20 individual VirE2 aggregates plotted to a common origin.

Embodiment 7: FIG. 7 Illustrated Effects of Myosin-Tail Overexpressions on VirE2 Trafficking FIG. 7 illustrated effects of myosin-tail overexpressions on VirE2 trafficking. *A. tumefaciens* EHA105virE2::GFP11 cells harboring a binary plasmid which encodes a tail fragment of respective myosins downstream of 35S promoter were infiltrated into transgenic *N. benthamiana* (Nb308A) leaves expressing both GFP1-10 and DsRed. The leaf epidermal cells were observed at 2 d post agroinfiltration under confocal microscope with UPLSAPO×60 N.A. 1.20 water immersion objective. Red, free DsRed; Green, VirE2-GFP$_{comp}$. (a) Schematic presentations of different myosin-tail constructs that were introduced into tobacco cells. (b) Western analysis of leaf samples agroinfiltrated with myosin tail constructs. EV, empty vector control. Myosin tails were HA tagged. GFP1-10 was detected to assess the amount of sample loaded, as shown in the lower panel. (c) Effects of myosin tail overexpressions on VirE2 trafficking. Z-slices were captured with 0.5 μm step. Extended focus image was shown. Scale bar represents 20 μm. The movement tracking of 20 individual VirE2 aggregates plotted to a common origin is shown below the figure.

Embodiment 8: FIG. 8 Illustrated a Time-Lapse Imaging of a NLS1-Mutant VirE2 Moving on an Endoplasmic Reticulum Strand FIG. 8 illustrated a time-lapse imaging of a NLS1-mutant VirE2 moving on an endoplasmic reticulum strand. EHA105virE2Δnls1 (amino acids 221KLR . . . KYGRR237 were replaced by alanine) cells were infiltrated into transgenic *N. benthamiana* (Nb308ER) leaves constitutively expressing ER-mCherry and GFP1-10. Relative time is shown at the top right. Scale bar represents 10 μm.

Embodiment 9: FIG. 9 Illustrated Effects of ML-7 Treatment on Root Tumorigenesis Assay FIG. 9 illustrated effects of ML-7 treatment on root tumorigenesis assay. Root segments from 10-day old wild type *A. thaliana* seedlings were infected with a tumor inducing *Agrobacterium* stain A348. Tumors were photographed three weeks later. (a) Tumors formed with or without ML-7 treatment. ML-7 was added (10 μM) into the col-cultivation mixture and then washed off when the root segments were transferred onto new plates for tumor formation. (b) Tumorigenesis efficiency as determined by percentage of root segments with tumors. (c) Effect of ML-7 on root segment viability. (d) Effect of ML-7 on *Agrobacterium* viability

Embodiment 10: FIG. 10 Illustrated Effects of RNAi Silencing of XI-2 and XI-K on Tumor Formation FIG. 10 illustrated effects of RNAi silencing of XI-2 and XI-K on tumor formation. Wild type *N. benthamiana* plants were agroinfiltrated with respective RNAi constructs. The mRNA analysis and agroinfection was conducted three weeks later. (a) Leaf disc tumors with respective genes silenced by RNAi. (b) The mRNA levels of respective genes in silenced plants as detected by real-time PCR. (c) Average fresh weight of leaf discs with tumors.

Embodiment 11: FIG. 11 Illustrated an Effect of a Drug on VirE2 Movement

FIG. 11 illustrated an effect of a drug on VirE2 movement. *A. tumefaciens* EHA105virE2::GFP11 cell was injected and infiltrated into a transgenic tobacco line Nb308A constantly expressing a GFP1-10 and a DsRed. The drug was injected and infiltrated into a leaf six hours before observation. Two days after the injection and infiltration of *A. tumefaciens*, leaf epidermal cells were placed under a confocal microscope to be observed with a UPLSAPO x60 N.A. 1.20 water immersion lens. The red was a free DsRed; and the green was a VirE2-GFPcomp. A Z-multilayer slice image was acquired with 0.5 μm per step. The diagram in the upper row was a common origin diagram of movement tracks of 20 VirE2 polymers. The diagram in the lower row illustrated an average speed of the 20 VirE2 polymers in movement.

Although the present invention has been described to a certain extent, it is obvious that appropriate changes in various conditions can be made without departing from the spirit and scope of the present invention. It can be understood that the present invention is not limited to the embodiments, but falls within the scope of the claims, which includes the equivalent replacement of each of the factors.

The invention claimed is:

1. A method for observing an effect of a compound and/or a drug on cells in real time, wherein the method comprises the following steps of:
   introducing a marker for observing an effect of a compound and/or a drug on cells in real time or enabling the cells to contain a marker for observing an effect of a compound and/or a drug on cells in real time, or the marker, wherein the marker is
   the amino acid sequences shown in SEQ ID NO:1 and SEQ ID NO:2;
   adding the compound and/or the drug into the cells; and
   observing a morphology, a movement track and/or a speed of the marker in the cells in real time;
   wherein the morphology of the marker comprises a size, a shape, a movement mode and/or a position of a filamentous structure formed by a VirE2-GFP;
   wherein the observing an effect of a compound and/or a drug on cells in real time is to observe a movement of a VirE2-GFP on an endoplasmic reticulum/actin network in real time.

2. The method according to claim 1, wherein the cells are selected from plant cells, yeasts, fungi, green algae or animal cells.

3. The method according to claim 1, wherein the compound and/or the drug comprises a nucleotide and/or a small molecule drug.

4. The method according to claim 1, wherein the effect is a nonspecific toxicity of the compound and/or the drug.

* * * * *